United States Patent [19]

Hillman et al.

[11] Patent Number: 5,856,129
[45] Date of Patent: Jan. 5, 1999

[54] DNA ENCODING A HUMAN PURINOCEPTOR

[75] Inventors: Jennifer L. Hillman, San Jose; Roger Coleman, Mountain View, both of Calif.

[73] Assignee: Incyte Pharmaceuticals, Inc., Palo Alto, Calif.

[21] Appl. No.: 742,621

[22] Filed: Oct. 30, 1996

[51] Int. Cl.[6] .......................... C12N 15/12; C07K 14/705
[52] U.S. Cl. .................. 435/69.1; 435/252.3; 435/254.1; 435/320.1; 435/325; 536/23.5; 536/24.31
[58] Field of Search ................................ 536/23.5, 24.31; 435/69.1, 320.1, 325, 252.3, 254.11

[56] References Cited

FOREIGN PATENT DOCUMENTS

WO 9533048  12/1995  WIPO.
WO 8741222  11/1997  WIPO.

OTHER PUBLICATIONS

Grazia–Guzman, M., et al., "Characterization of Recombinant Human P2X$_4$ Receptor Reveals Pharmacological Differences to the Rat Homologue," *Molecular Pharmacology*, 51:109–118 (1997).

Xuenong, B., et al., "A P2x purinoreceptor cDNA conferring a novel pharmacological profile," *FEBS Letters*, 375:129–133 (1995).

Soto, F., et al., "P2X$_4$: An ATP–activated ionotropic receptor cloned from rat brain," *Proc. Natl. Acad. Sci. USA*, 93:3684–3688 (1996).

Wang, C., et al., "Cloning and Pharmacological characterization of a fourth P2X Receptor Subtype Widely Expressed in Brain and Peripheral Tissues including Various Endocrine Tissues," *Biochemical and Biophysical Research Communications*, 220;196–202 (1996).

Burnstock, G., "Purinegenic Mechanisms", *Ann.NY Acad. Sci.* (1990) 603:1–17.

Bean, B.P., "Pharmacology and electrophysiology of ATP–activated ion channels" *Trends Pharmac. Sci.* (1992) 12:87–90.

Bean, B.P. et al., "ATP–activated channels in excitable cells" *Ion Channels* (1990) 2:169–203.

Barnard, E.A., et al., "G protein–coupled receptors for ATP and other nucleotides: a new receptor family" *Trends Pharmac. Sci.* (1994) 15:67–71.

Burnstock, G., "Sympathetic purinergic transmission in small blood vessels" *Trends Pharmac. Sci.* (1988) 9:116–7.

Evans, J.R. et al., "Vasoconstriction of guinea–pig submucosal arterioles following sympathetic nerve stimulation is mediated by the release of ATP" *Br. J. Pharmacol.* (1992) 106:242–9.

Suprenant, A. et al., "The Cytolytic P$_{2Z}$ Receptor for Extracellular ATP Idenfified as a P$_{2X}$ Receptor (P2X$_7$)" *Science* (1996) 272:735–738.

Baricordi, O.R. et al, "An ATP–Activated Channel is Involved in Mitogenic Stimulation of Human T Lymphocytes" *Blood* (1996) 87:682–90.

Chused, T.M. et al., "Murine T Lymphocytes Modulate Activity of an ATP–Activated P$_{2Z}$–Type Purinoceptor During Differentiation" *The Journal of Immunology* (1996) 157:1371–80.

Erlinge, D. et al., "Characterization of an ATP receptor mediating mitogenesis in vascular smooth muscle cells" *Eur. J. Pharmacol.* (1995) 289:135–49.

Soslau, G. et al., "Extracellular ATP inhibits agonist–induced mobilization of internal calcium in platelets", *Biochemica et Biophysica Acta* (1995) 1268:73–80.

Valera, S. et al., "A new class of ligand–gated ion channel defined by P$_{2X}$ receptor for extracellular ATP", *Nature* (1994) 371:516–519.

Brake, A.J. et al., "New structural motif for ligand–gated ion channels defined by an ionotropic ATP receptor" *Nature* (1994) 371:519–523.

Valera, S. et al., "Characterization and Chromosomal Localization of a Human P$_{2X}$ Receptor from the Urinary Bladder" *Receptors and Channels* (1995) 3:283–289.

Longhurst, P.A. et al., "The human P$_{2X1}$ receptor: molecular cloning, tissue distribution, and location to chromosome 17" *Biochimica et Biophysica Acta* (1996) 1308:185–188.

Owens, G.P. et al., "Identification of mRNAs Associated with Programmed Cell Death in Immature Thymocytes" *Molecular and Cellular Biology* (1991) 11:4177–4188.

Nakazawa, K. et al., "An ATP–activated conductance in pheochromocytoma cells and its suppression by extracellular calcium" *Journal of Physiology* (1990) 428:257–272.

Majid, M.A. et al., "Characterization of ATP receptor which mediates norepinephrine release in PC12 cells" *Biochemica et Biophysica Acta* (1992) 1136:283–289.

Fieber, L.A. et al., "Adenosine triphosphate–evoked currents in cultured neurones dissociated from rat parasympathetic cardiac ganglia" *Journal of Physiology* (1991) 434:239–256.

Cloues, R. et al., "Zn$^{2+}$ potentiates ATP–activated currents in rat sympathetic neurons" *European Journal of Physiology* (1993) 424:152–158.

(List continued on next page.)

*Primary Examiner*—Sally P. Teng
*Attorney, Agent, or Firm*—Lucy J. Billings; Incyte Pharmaceuticals, Inc.

[57] ABSTRACT

The present invention provides a novel human P$_{2X}$ purinoreceptor (HPURR) and polynucleotides which identify and encode HPURR. The invention also provides genetically engineered expression vectors and host cells comprising the nucleic acid sequences encoding HPURR and a method for producing HPURR. The invention also provides for use of HPURR, and agonists, antibodies or antagonists specifically binding HPURR, in the prevention and treatment of diseases associated with expression of HPURR. Additionally, the invention provides for the use of antisense molecules to polynucleotides encoding HPURR for the treatment of diseases associated with the expression of HPURR. The invention also provides diagnostic assays which utilize the polynucleotide, or fragments or the complement thereof, and antibodies specifically binding HPURR.

8 Claims, 11 Drawing Sheets

OTHER PUBLICATIONS

Friel, David D., "An ATP–sensitive conductance in single smooth muscle cells from the rat vas deferens" *Journal of Physiology* (1988) 401:361–380.

Evans, R.J. et al., "ATP mediates fast synaptic transmission in mammalian neurons" *Nature* (1992) 357:503–505.

Benham, C.D. et al., "A novel receptor–operated $Ca^{2+}$–permeable channel activated by ATP in smooth muscle" *Nature* (1987) 328:275–278.

Saraste, M. et al., "The P–loop—a common motif in ATP–and GTP–binding proteins" *TIBS 15* (1990) 430–434.

Bo et al., FEBS Letters, 375, 129–183, Nov. 1995.

Grandy et al., Proc. Natl. Acad. Sci., 86, 9762–9766, 1989.

```
5' TCG ACC CAC GCG TCC GGC GCG GCC ATG GCG GGC TGC TGC GCC GCG CTG GCG   54
                                    M   A   G   C   C   A   A   L   A
            9          18          27          36          45          54

GCC TTC CTG TTC GAG TAC GAC ACG CCG CGC ATC GTG CTC ATC CGC AGC CGC AAA  108
    A   F   L   F   E   Y   D   T   P   R   I   V   L   I   R   S   R   K
           63          72          81          90          99         108

GTG GGG CTC ATG AAC CGC GCC GTG CAA CTG CTC ATC CTG GCC TAC GTC ATC GGG  162
    V   G   L   M   N   R   A   V   Q   L   L   I   L   A   Y   V   I   G
          117         126         135         144         153         162

TGG GTG TTT GTG TGG GAA AAG GGC TAC CAG GAA ACT GAC TCC GTG GTC AGC TCC  216
    W   V   F   V   W   E   K   G   Y   Q   E   T   D   S   V   V   S   S
          171         180         189         198         207         216

GTT ACG ACC AAG GTC AAG GGC GTG GCT GTG ACC TAC CAG GAA AAA CTT GGA TTC  270
    V   T   T   K   V   K   G   V   A   V   T   Y   Q   E   K   L   G   F
          225         234         243         252         261         270

CGG ATC TGG GAT GTG GCG GAT TAT GTG ATA CCA GCT CAG GAG GAA AAC TCC CTC  324
    R   I   W   D   V   A   D   Y   V   I   P   A   Q   E   E   N   S   L
          279         288         297         306         315         324

TTC GTC ATG ACC AAC GTG ATC CTC ACC ATG AAC CAG ACA CAG GGC CTG TGC CCC  378
    F   V   M   T   N   V   I   L   T   M   N   Q   T   Q   G   L   C   P
          333         342         351         360         369         378
```

FIGURE 1A

```
GAG ATT CCA GAT GCG ACC ACT GTG TGT AAA TCA GAT GCC AGC TGT ACT GCC GGC
 E   I   P   D   A   T   T   V   C   K   S   D   A   S   C   T   A   G
387         396         405         414         423         432

TCT GCC GGC ACC CAC AGC AAC GGA GTC TCA ACA GGC AGG TGC GTA GCT TTC AAC
 S   A   G   T   H   S   N   G   V   S   T   G   R   C   V   A   F   N
441         450         459         468         477         486

GGG TCC GTC AAG ACG TGT GAG GTG GCG GCC TGG TGC CCG GTG GAG GAT GAC ACA
 G   S   V   K   T   C   E   V   A   A   W   C   P   V   E   D   D   T
495         504         513         522         531         540

CAC GTG CCA CAA CCT GCT TTT TTA AAG GCT GCA GAA AAC TTC ACT CTT TTG GTT
 H   V   P   Q   P   A   F   L   K   A   A   E   N   F   T   L   L   V
549         558         567         576         585         594

AAG AAC ATC TGG ATT TAT CCC AAA TTT AAT TTC AGC AAG AGG AAT ATC CTT CCC
 K   N   I   W   I   Y   P   K   F   N   F   S   K   R   N   I   L   P
603         612         621         630         639         648

AAC ATC ACC ACT ACT TAC CTC AAG TCG TGC ATT TAT GAT GCT AAA ACA GAT CCC
 N   I   T   T   T   Y   L   K   S   C   I   Y   D   A   K   T   D   P
657         666         675         684         693         702

TTC TGC CCC ATA TTC CGT CTT GGC AAA ATA GTG GAG AAC GCA GGA CAC AGT TTC
 F   C   P   I   F   R   L   G   K   I   V   E   N   A   G   H   S   F
711         720         729         738         747         756
```

FIGURE 1B

```
     765           774           783           792           801           810
CAG GAC ATG GCC GTG GAG GGA GGC ATC ATG GGC ATC CAG GTC AAC TGG GAC TGC
 Q   D   M   A   V   E   G   G   I   M   G   I   Q   V   N   W   D   C 819           828           837           846           855           864
AAC CTG GAC AGA GCC GCC TCC CTC TGC TTG CCC AGG TAC TCC TTC CGC CGC CTC
 N   L   D   R   A   A   S   L   C   L   P   R   Y   S   F   R   R   L 873           882           891           900           909           918
GAT ACA CGG GAC GTT GAG CAC AAC GTA TCT CCT GGC TAC AAT TTC AGG TTT GCC
 D   T   R   D   V   E   H   N   V   S   P   G   Y   N   F   R   F   A 927           936           945           954           963           972
AAG TAC AGA GAC CTG GCT GGC AAC GAG CAG CGC ACG CGC ATC AAG GCC TAT
 K   Y   R   D   L   A   G   N   E   Q   R   T   R   I   K   A   Y 981           990           999          1008          1017          1026
GGC ATC CGC TTC GAC ATC ATT GTG TTT GGG AAG GCA CTC ACG CTC ATC GAC ATC
 G   I   R   F   D   I   I   V   F   G   K   A   L   T   L   I   D   I 1035          1044          1053          1062          1071          1080
CCC ACT ATG ATC AAC ATC GGC TCT GGC CTG GCA CTG CTA GGC ATG GCG ACC GTG
 P   T   M   I   N   I   G   S   G   L   A   L   L   G   M   A   T   V 1089          1098          1107          1116          1125          1134
CTG TGT GAC ATC ATA GTC CTC TAC TGC ATG AAG AAA AGA CTC TAC TAT CGG GAG
 L   C   D   I   I   V   L   Y   C   M   K   K   R   L   Y   Y   R   E
```

FIGURE 1C

```
       1143            1152            1161            1170            1179            1188
AAG AAA TAT AAA TAT GTG GAA GAT TAC GAG CAG GGT CTT GCT AGT GAG CTG GAC
 K   K   Y   K   Y   V   E   D   Y   E   Q   G   L   A   S   E   L   D 1197            1206            1215            1224            1233            1242
CAG TGA GGC CTA CCC CAC ACC TGG GCT CTC CAC AGC CCC ATC AAA GAA CAG AGA
 Q   *   G   L   P   H   T   W   A   L   H   S   P   I   K   E   Q   R 1251            1260            1269            1278            1287            1296
GGA GGA GGG AGA AAT GGC CAC CAC ATC ACC CCA GAG AAA TTT CTG GAA TCT
 G   G   G   R   N   G   H   H   I   T   P   E   K   F   L   E   S 1305            1314            1323            1332            1341            1350
GAT TGA GTT TCC ACT CCA CAA GCA CTC AGG GTT CCC CAG CAG CTC CTG TGT GTT
 D   *   V   S   T   P   Q   A   L   R   V   P   Q   Q   L   L   C   V 1359            1368            1377            1386            1395            1404
GTG TGC AGG ATT TGT CTT TTG CCC ACT CGG CCC AGG AGG TCA GCA GTC TGT TCT TGG
 V   C   R   I   C   L   L   P   T   R   P   R   R   S   A   V   C   S   W 1413            1422            1431            1440            1449            1458
CTG GGT CAA CTT TGC TTT TCC CGC AAC CTG GGG TTG TCG GGG GAG CGC TGG CCC
 L   G   Q   L   C   F   S   R   N   L   G   L   S   G   E   R   W   P 1467            1476            1485            1494            1503            1512
GAC GCA GTG GCA CTG CTG TGG CTT TCA GGG CTG GAG CTG GCT TTG TTC AGA AGC
 D   A   V   A   L   L   W   L   S   G   L   E   L   A   L   F   R   S
```

FIGURE 1D

```
      1521             1530             1539             1548             1557             1566
CTC CTG TCT CCA GCT CTT TAC AGG ACA GGC CCA GTC CTT TGA GGC ACG GCG GCT
 L   L   S   P   A   L   Y   R   T   G   P   V   L   *

1575             1584             1593             1602             1611             1620
CTG TTC AAG CAC TTT ATG CGG CAG GGG AGG CCG CCT GGC TGC AGT CAC TAG ACT 1629             1638             1647             1656             1665             1674
TGT AGC AGG CCT GGG CTG CAG GCT TCC CCC CGA CCA TTC CCT GCA GCC ATG CGG 1683             1692             1701             1710             1719             1728
CAG AGC TGG CAT TTC TCC TCA GAG AAG CGC TGT GCT AAG GTG ATC GAG GAC CAG 1737             1746             1755
ACA TTA AAG CGT GAT TTT CTT AAA AAA AAA AAA AAA A 3'
```

```
176 P A F L K A A E N F T L L V K N N I W Y P K F N F S K R N I   HPURR
176 P A L L R E A E N F T L F I H N S F P P R F K V N R R N L   g1166438
176 P A L L R E A E N F T L F I H N S F P R F K V N R R N L   g558240
174 H F L G K M A P N F T I L H Y P K F S K G N I   g558831

206 L P N I T T Y L K S C I Y D A K T D P F C P I F R L G K I   HPURR
206 V E E V N A A H M K T L F H K T L H P L C P V F Q L G Y V   g1166438
206 V E E V N G T Y M K K I Q H P L C P V F N L G Y V   g558240
204 A S Q - K S D Y L K H C T F D Q D S D P Y C P I F R L G F I   g558831

236 V E N A G H S F O D M A V E G G I M G I Q V N W D C N L D R   HPURR
236 V Q E S G Q Q N F S T L A E K G G V V G I T H I D D W H C D L   g1166438
236 V R E S G Q F R S L A H K G G V V G I T H I D W K C D L   g558240
233 V E K A G E N F T E L A H H K G G V I G I H I N W N C D L   g558831

266 A A S L C L P R Y S F R R L D T R D V E H N V S P G Y N F R   HPURR
266 H V R H C R P H Y E F F H G L Y E - - - E K N L S P G F N F R   g1166438
266 H V R H C R P I Y Q F H G L Y G - - - D P A S S G Y N F R   g558240
263 S E S C N P K Y S F R R L D P K Y - - - I   g558831

296 F A K Y Y R D L A G N E O R T L I K A Y G I R F D I I V F G   HPURR
293 F A R R H F V E - N G T N Y R R H L F K K V F G I H L V D D G   g1166438
293 F A R R H F V Q - N G T N R R H L F V F G I H F D L V D G   g558240
291 F A K Y Y K I N G T T T R T L I K A Y G I H I D V H G   g558831

326 K A G K F D I I P T M I N I G S G L A L L G M A T V L C D I   HPURR
322 K A G K F D I I H I P T M T T H I G S G I F F G V A T V L C D L   g1166438
322 K A G K F D I I H I P T M T T H I G S G I F F G V A T V L C D L   g558240
321 Q A G K F S L H P T I H N L A T A L T S I G V G S F L C D W   g558831
```

FIGURE 2B

```
                                                                              HPURR
     I V L Y C M K K R L Y Y R E K K Y K - - - - - - - - - - -                g1166438
     L L L H I L P K R Y Y K K F K - - - - - - - - - - -                      g558240
     L L L T F M N K L Y S H K K D - - - - - - - - - R W                      g558831
356  I V L Y C M K K R L Y Y R E K K Y K - - - - - - - - - - -                HPURR
352  L L L H I L P K R Y Y K K F K - - - - - - - - - - -                      g1166438
352  L L L H I L P K R Y Y K K F K - - - - - - - - - - -                      g558240
351  L L L T F M N K L Y S H K K F D K V R T P K H P S S R W                  g558831

HPURR
     - - - - - - - - - - - - - - -                                            g1166438
     - - Y V E D Y E Q P K - - - -                                            g558240
     - - Y A E D M G P - - - - -                                              g558831
374  - - - - - - - - - - - - - - -                                            HPURR
370  - - Y V E D Y E Q P K - - - -                                            g1166438
370  - - Y A E D M G P - - - - -                                              g558240
370  - - Y A E D M G P - - - - -                                              
381  P V T L A L V L G Q I P P P S H Y S Q D Q P P S P P S G E

HPURR
     - - - - - - - - - - - - - - - -                                          g1166438
381  - G L A S E A E R D L A A T S S - - - - - - - -                          
377  - G A A E E G E H D P V A T S S - - - - - - - -                          g558240
377  - G G E G E G A H L P L A V Q S - - - - - - - -                          g558831
411  G P T L G Q H M G Q R P P V P E P S Q Q D S T D P K G L A

HPURR
386  - - L D Q E N M R T S - - - - - - - -                                    g1166438
389  - T L G Q E N M R T S - - - - - - - -                                    g558240
389  - T L G Q H M G Q R P P V P E P S Q Q D S T D P K G L A                  g558831
441  D T L G Q H I S A L T E Q V V

388                                                                           HPURR
399                                                                           g1166438
399                                                                           g558240
471  Q L                                                                      g558831
```

FIGURE 2C

| Library | Lib Description | Abun | Pct Abun |
|---|---|---|---|
| SYNORAT04 | synovium, wrist, rheumatoid, 62 F | 4 | 0.0695 |
| MPHGLPT02 | macrophages (adher PBMNC), M/F, treated LPS | 1 | 0.0492 |
| COLNNOT01 | colon, 75 M, match to COLNTUT02 | 2 | 0.0426 |
| PITUNOT01 | pituitary, 16-70 M/F, | 1 | 0.0423 |
| MUSCNOT02 | muscle, psoas, 12 M | 1 | 0.0381 |
| SYNORAT05 | synovium, knee, rheumatoid, 62 F | 2 | 0.0338 |
| BRSTTUT01 | breast tumor, 55 F, match to BRSTNOT02 | 2 | 0.0301 |
| LUNGNOT12 | lung, 78 M | 1 | 0.0277 |
| BMARNOT02 | bone marrow, 16-70 M/F | 1 | 0.0269 |
| KIDNNOT09 | kidney, fetal M | 1 | 0.0266 |
| COLNTUT02 | colon tumor, 75 M, match to COLNNOT01 | 1 | 0.0220 |
| SCORNOT01 | spinal cord, 71 M | 1 | 0.0200 |
| KIDNNOT05 | kidney, neonatal F | 1 | 0.0161 |
| CORPNOT02 | brain, corpus callosum, Alzheimer's, 74 M | 1 | 0.0152 |
| COLNFET02 | colon, fetal F | 1 | 0.0142 |
| THYRNOT03 | thyroid tumor, adenoma, 28 F | 1 | 0.0138 |
| UCMCL5T01 | mononuclear cells, treated IL-5 | 1 | 0.0125 |

FIGURE 5

DNA ENCODING A HUMAN PURINOCEPTOR

FIELD OF THE INVENTION

This invention relates to nucleic acid and amino acid sequences of a novel human $P_{2X}$ purinoreceptor and to the use of these sequences in the diagnosis, prevention, and treatment of disorders and diseases of the immune system, nervous system, cardiovascular system, and of smooth muscle.

BACKGROUND OF THE INVENTION

Adenosine 5'-triphosphate (ATP) has many different physiological functions in the cell. For example, ATP is the energy source for many biochemical reactions, a precursor for ribonucleic acid (RNA) synthesis, the precursor for cyclic AMP synthesis, etc. ATP also functions as an extracellular messenger in neuronal and non-neuronal tissues. Extracellular ATP exerts its effects on these tissues by acting through membrane-associated purinoreceptors (Burnstock, G. Ann. NY Acad. Sci. (1990) 603:1–17). The purinoreceptors can be either ligand-gated ion channels (Bean, B. P. (1992) Trends Pharmac. Sci. 12:87–90; Bean, B. P. and Fried, D. D. (1990) Ion Channels 2:169–203) that are generally referred to as $P_{2X}$ receptors, (but also known as: purinergic channels, $P_{2X}$R-channels, and ATP-gated channels) or G-protein-coupled ($P_{2Y}$ or $P_{2U}$) receptors (Barnard, E. A. et al. (1994) Trends Pharmac. Sci. 15:67–70).

ATP-gated $P_{2X}$ receptors have been identified on autonomic and sensory neurons and on smooth muscle cells where they mediate membrane depolarization and, in certain cases, $Ca^{2+}$ flux (Bean, B. P., supra). The $P_{2X}$ receptors are present on both nerve terminals and cell bodies of peripheral (PNS) and central (CNS) neurons. The receptors have short latency and inactivation time-constants that are consistent with a physiological role in neurotransmission. Their function includes fast signaling across synapses of the PNS and CNS. In the CNS, where ATP acts as a fast excitatory synaptic transmitter at nerve—nerve synapses, $P_{2X}$ receptors may mediate rapid sensory, motor, and cognitive functions. ATP may also serve as a co-transmitter of acetylcholine, substance P, and noradrenaline signals.

Peripheral $P_{2X}$ receptors also regulate effector structures such as cardiac and smooth muscle (Burnstock, G., supra), and are responsible for sympathetic vasoconstriction in small arteries and arterioles (Burnstock, G. (1988) Trends Pharmac. Sci. 9:116–7; Evans, J. R. and Surprenant, A. (1992) Br. J. Pharmacol. 106:242–9). In muscle and other cells, $P_{2X}$ receptors exert effects via direct conductance of $Ca^{2+}$ ions as well as via conductance of $Na^+$ ions; $Na^+$ conductance causes membrane depolarization and subsequent activation of voltage-gated neuronal $Na^+$ channels. $Ca^{2+}$ influx through ATP-gated channels may also have a role in neurosecretory processes where the effector is a gland.

$P_{2X}$ receptors also have several roles in immune system responses. A purinoreceptor, originally designated $P_{2Z}$, has been cloned and identified as a member of the $P_{2X}$ family (Surprenant, A. et al. (1996) Science 272:735–738). This $P_{2X}$ receptor, expressed in both rat brain and macrophages, is responsible for ATP-dependent lysis of antigen-presenting macrophages. ATP-gated channels are involved in mitogenic stimulation of human T-cells, and extracellular ATP exerts a synergistic effect on DNA synthesis stimulated by T-cell-specific mitogens such as phytohemagglutinin (Baricordi, O. R. et al. (1996) Blood 87:682–90). ATP can also mediate differentiation and cell death (apoptosis) of thymocytes and peripheral T cells (Chused, T. M. et al. (1996 J. Immunol) 157:1371–80). Other effects of extracellular ATP include mitogenesis of vascular smooth muscle cells (Erlinge, D. et al. (1995) Eur. J. Pharmacol. 289:135–49), and inhibition of platelet aggregation and clot size (Soslau, G. et al. (1995 Biochim. Biophys. Acta) 1268:73–80).

Ion channels gated by extracellular ligands such as nicotinic acid, serotonin, GABA, glycine or the excitatory amino acids all share common features and topology. Because of the functional similarities between those receptors and the ATP-gated $P_{2X}$ receptors, there was an expectation that the latter would also share common structural features. Cloning of $P_{2X}$ receptors from rat (Valera, S. et al.(1995) Nature 371:516–9; Brake, A. J. et al, supra) and human (Valera, S. et al.(1995) Recept. Channels 3:283–9; Longhurst, P. A. et al.(1996) Biochim. Biophys. Acta 1308:185–8) demonstrates that the $P_{2X}$ receptors comprise a separate and distinct family of ion channels. However, the sequences of cloned $P_{2X}$ cDNAs (Valera, S. et al, Nature, supra; Brake, A. J. et al, supra) have homology to the RP-2 partial cDNA clone previously identified by Owens G. P. (1991; J. Molec. Cell Biol. 11:4177–88). The RP-2 gene is activated in thymocytes which have been induced to undergo apoptosis. Such activation of RP-2 is consistent with a role for ATP and $P_{2X}$ receptors in programmed cell death.

Numerous $P_{2X}$ receptors have been cloned from the rat and are distinguishable pharmacologically by their responses to various ATP analogs such as α,β-methylene-ATP, β,γ-methylene-ATP, 2-methyl-thio-ATP, and γ-thio-ATP. For example, when cloned rat $P_{2X}$ receptor g558831 (SEQ ID NO:5) is expressed in Xenopus oocytes, 2-methyl-thio-ATP and γ-thio-ATP are roughly equivalent agonists, whereas α,β-methylene-ATP and β,γ-methylene-ATP are inactive as either agonists or antagonists ( Brake, A. J. et al.(1995) Nature 371:519–23). This profile is similar to that of native $P_{2X}$ receptors expressed by rat PC12 cells and some sensory and autonomic neurons (Nakazawa, K. et al.(1990) J. Physiol. 428:257–72; Majid, M. A. et al.(1992) Biochim. Biophys. Acta 1136:283–289; Fieber, L. A. and Adams, D. J. (1991) J. Physiol. 434:239–56; Cloues, R. et al.(1993) Pflug. Archiv 424:152–8), but differs from that of $P_{2X}$ receptors expressed by vascular smooth muscle, vas deferens, and some CNS neurons (Friel, D. D. (1988) J. Physiol. 401:361–80; Evans, R. J. et al.(1992) Nature 357:503–5; Benham, C. D. and Tsien, R. W. (1987) Nature 328:275–8).

At the molecular level, the $P_{2X}$ proteins are of variable length and have no significant homology with receptors outside of the family. The lack of an apparent amino terminal signal sequence suggests that both the N- and C-termini of the protein are cytoplasmic. There is a conserved loop, bounded by two hydrophobic putative transmembrane domains, that contains regularly spaced hydrophilic cysteine residues and likely resides on the outside of the cell membrane; all three potential N-linked glycosylation sites are within this loop. Extracellular ATP may bind to the loop in region(s) that resemble Walker type-A phosphate binding motifs (Saraste, M. et al.(1990) Trends Biochem. Sci. 15:430–4).

Northern blot analyses detect $P_{2X}$ messenger RNAs of varying sizes and relative abundances in adrenal gland, bladder, brain, intestines, lung, ovary, pituitary, retina, spinal cord, spleen, testis, thymus, and vas deferens, but fail to detect related sequences in liver or kidney (Valera, S. et al. Nature, supra; Brake, A. J. et al, supra.

The discovery of polynucleotides encoding novel human $P_{2X}$ purinoreceptors, and the molecules themselves, present the opportunity to investigate ATP-gated signal transduction. Discovery of molecules related to $P_{2X}$ purinoreceptors satisfies a need in the art by providing new diagnostic or therapeutic compositions useful in the diagnosis, prevention, and treatment of disorders and diseases of the immune system, nervous system, cardiovascular system, and of smooth muscle.

SUMMARY OF THE INVENTION

The present invention features a novel human purinoreceptor, hereinafter designated HPURR, and characterized as having similarity to $P_{2X}$ purinoreceptors isolated from human and rat.

Accordingly, the invention features a substantially purified HPURR having chemical homology to human and rat $P_{2X}$ purinoreceptors and the amino acid sequence of SEQ ID NO:1.

One aspect of the invention features isolated and substantially purified polynucleotides that encode HPURR. In a particular aspect, the polynucleotide is the nucleotide sequence of SEQ ID NO:2.

The invention also features a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HPURR. The present invention also features antibodies which bind specifically to HPURR, and pharmaceutical compositions comprising substantially purified HPURR. The invention also features use of agonists and antagonists of HPURR.

BRIEF DESCRIPTION OF THE FIGURES

FIG. 1 shows the amino acid sequence (SEQ ID NO:1) and nucleic acid sequence (SEQ ID NO:2) of HPURR. The alignment was produced using MacDNASIS PRO™ software (Hitachi Software Engineering Co., Ltd., San Bruno, Calif.).

FIG. 2 shows the amino acid sequence alignments among HPURR (SEQ ID NO:1), human $P_{2X}$ receptor (g1166438; SEQ ID NO:3), rat $P_{2X}$ receptor (g558240; SEQ ID NO:4), and rat $P_{2X}$ receptor (g558831; SEQ ID NO:5). Sequences were aligned using the multisequence alignment program of DNASTAR™ software (DNASTAR Inc, Madison Wis.).

FIG. 5 shows the northern analysis for SEQ ID NO:2. The northern analysis was produced electronically using LIFESEQ FL™ database (Incyte Pharmaceuticals, Inc., Palo Alto, Calif.).

DESCRIPTION OF THE INVENTION

Figure 3:
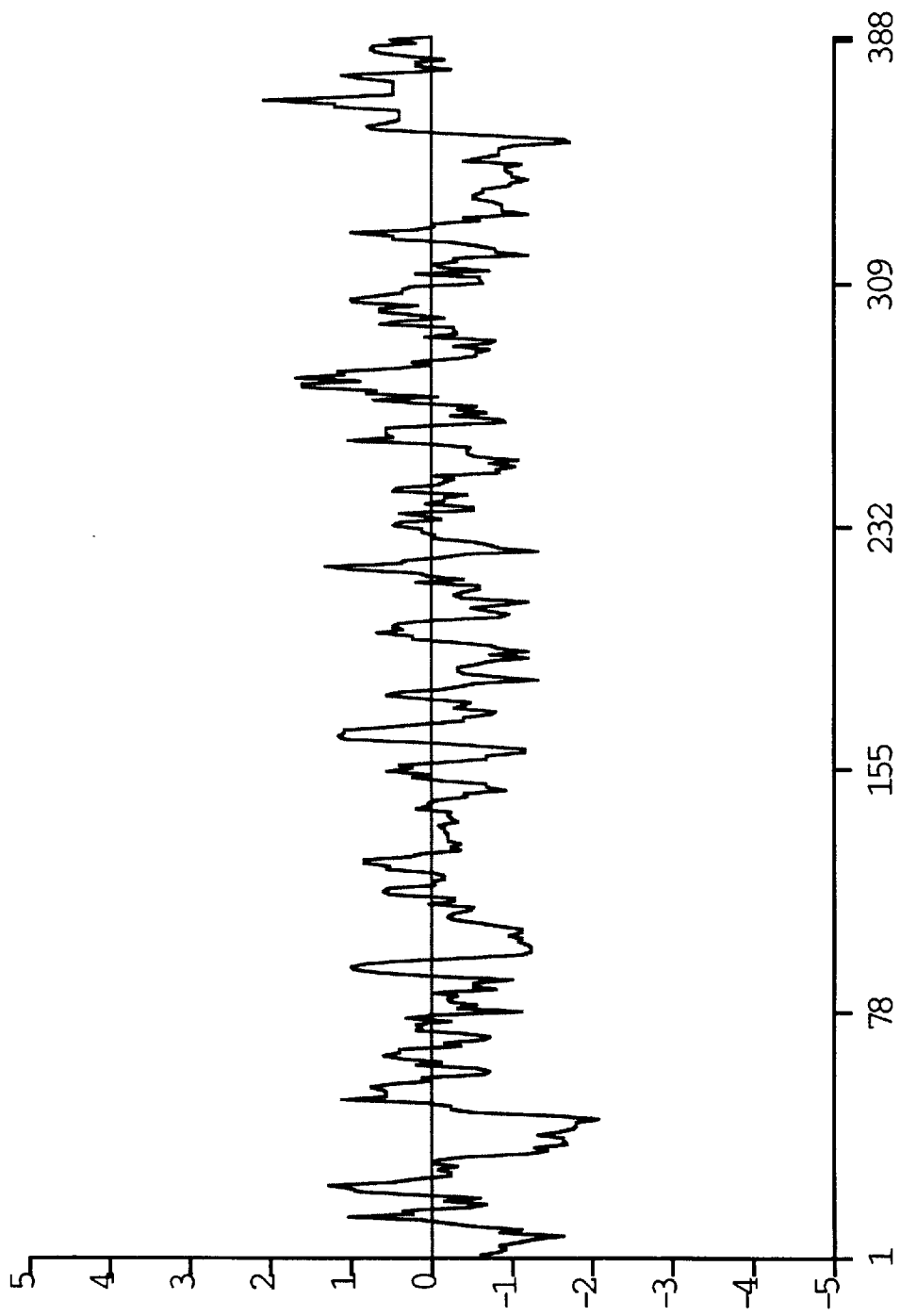
FIG. 3 shows the hydrophobicity plot (MacDNASIS PRO software) for HPURR, SEQ ID NO:1; the positive X-axis reflects amino acid position, and the negative Y-axis, hydrophobicity.

Before the present protein, nucleotide sequence, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HPURR, as used herein, refers to the amino acid sequences of substantially purified HPURR obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of HPURR, as used herein, refers to an amino acid sequence that is altered by one or more amino acids.

The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HPURR, or any oligopeptide thereof, to induce a specific immune response in appropriate animals or cells and to bind with specific antibodies.

The term "agonist", as used herein, refers to a molecule which, when bound to HPURR, causes a change in HPURR which modulates the activity of HPURR. Agonists may include proteins, nucleic acids, carbohydrates, or any other molecules which bind to HPURR.

The terms "antagonist" or "inhibitor", as used herein, refer to a molecule which, when bound to HPURR, modulates or blocks the biological or immunological activity of HPURR. Antagonists and inhibitors may include proteins, nucleic acids, carbohydrates, or any other molecules which bind to HPURR.

The term "modulate", as used herein, refers to a change or an alteration in the biological activity of HPURR. Modulation may be an increase or a decrease in protein activity, a change in binding characteristics, or any other change in the biological, functional or immunological properties of HPURR.

The term "mimetic", as used herein, refers to a molecule, the structure of which is developed from knowledge of the structure of HPURR or portions thereof and, as such, is able to effect some or all of the actions of $P_{2X}$ purinoreceptor-like molecules.

The term "derivative", as used herein, refers to the chemical modification of a nucleic acid encoding HPURR or the encoded HPURR. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and Dveksler, G. S. (1995) PCR Primer, a Laboratory Manual, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single-stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm–5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HPURR and fragments thereof. "Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HPURR or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection by northern analysis of the presence of ribonucleic acid that is related to SEQ ID NO:2 is indicative of the presence of mRNA encoding HPURR in a sample and thereby correlates with expression of the transcript encoding the protein.

"Alterations" in the polynucleotide of SEQ ID NO:2, as used herein, comprise any alteration in the sequence of polynucleotides encoding HPURR including deletions, insertions, and point mutations that may be detected using hybridization assays. Included within this definition is the detection of alterations to the genomic DNA sequence which encodes HPURR (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding HPURR (e.g., using fluorescent in situ hybridization (FISH) to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind HPURR polypeptides can be prepared using intact polypeptides or fragments containing small peptides of interest as the immunizing antigen. The polypeptide or peptide used to immunize an animal can be derived from translated RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human purinoreceptor (HPURR), the polynucleotides encoding HPURR, and the use of these compositions for the diagnosis, prevention, or treatment of disease.

Nucleic acids encoding the human HPURR of the present invention were first identified in Incyte Clone 555697 from a spinal cord DNA library (SCORNOT01) through a computer-generated search for amino acid sequence alignments. A consensus sequence, SEQ ID NO:2, was derived from the following overlapping and/or extended nucleic acid sequences: Incyte Clones 555697 (SCRONOT01) and 133269 (BMARNOT02).

Figure 2A:
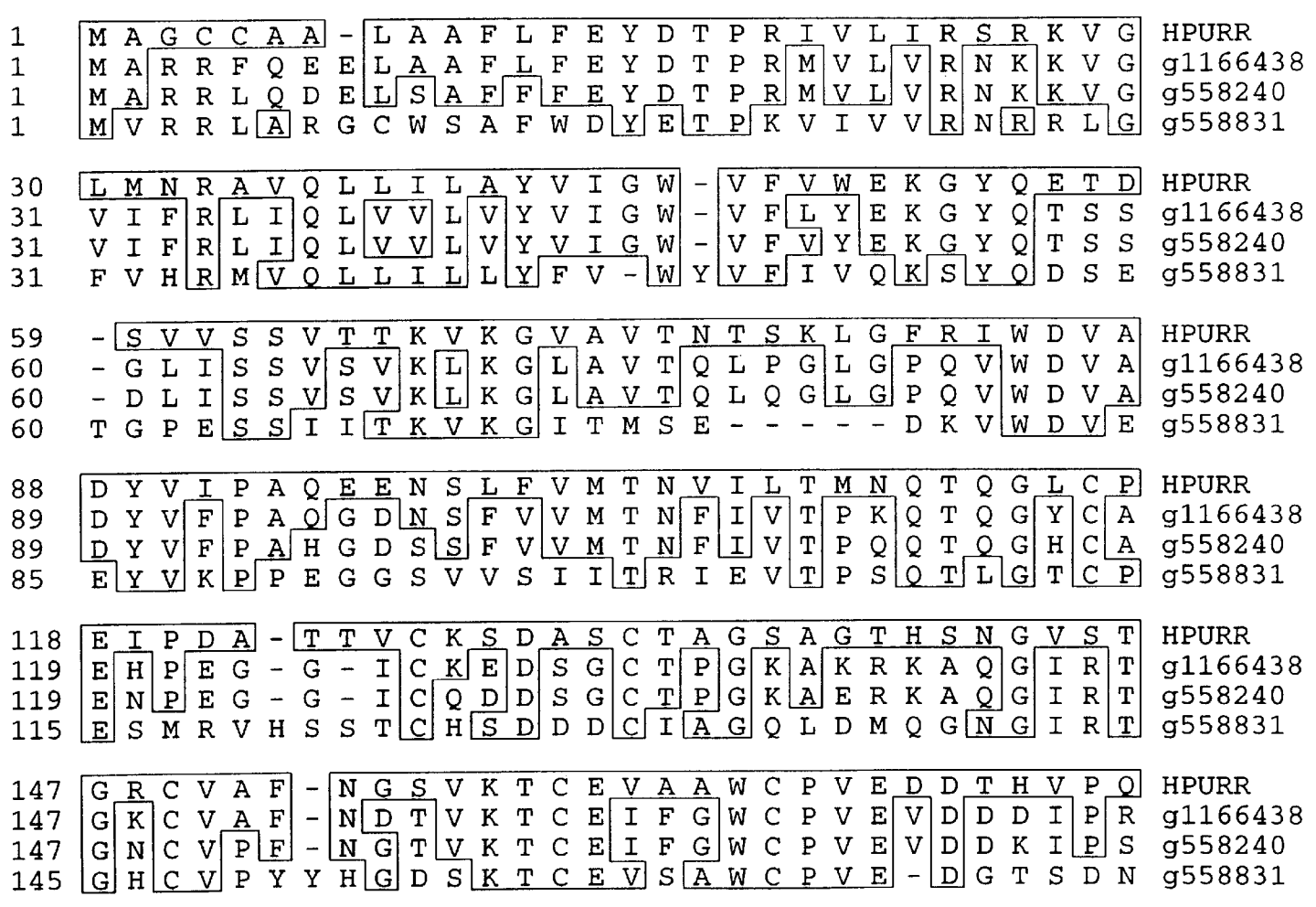
Figure 4:
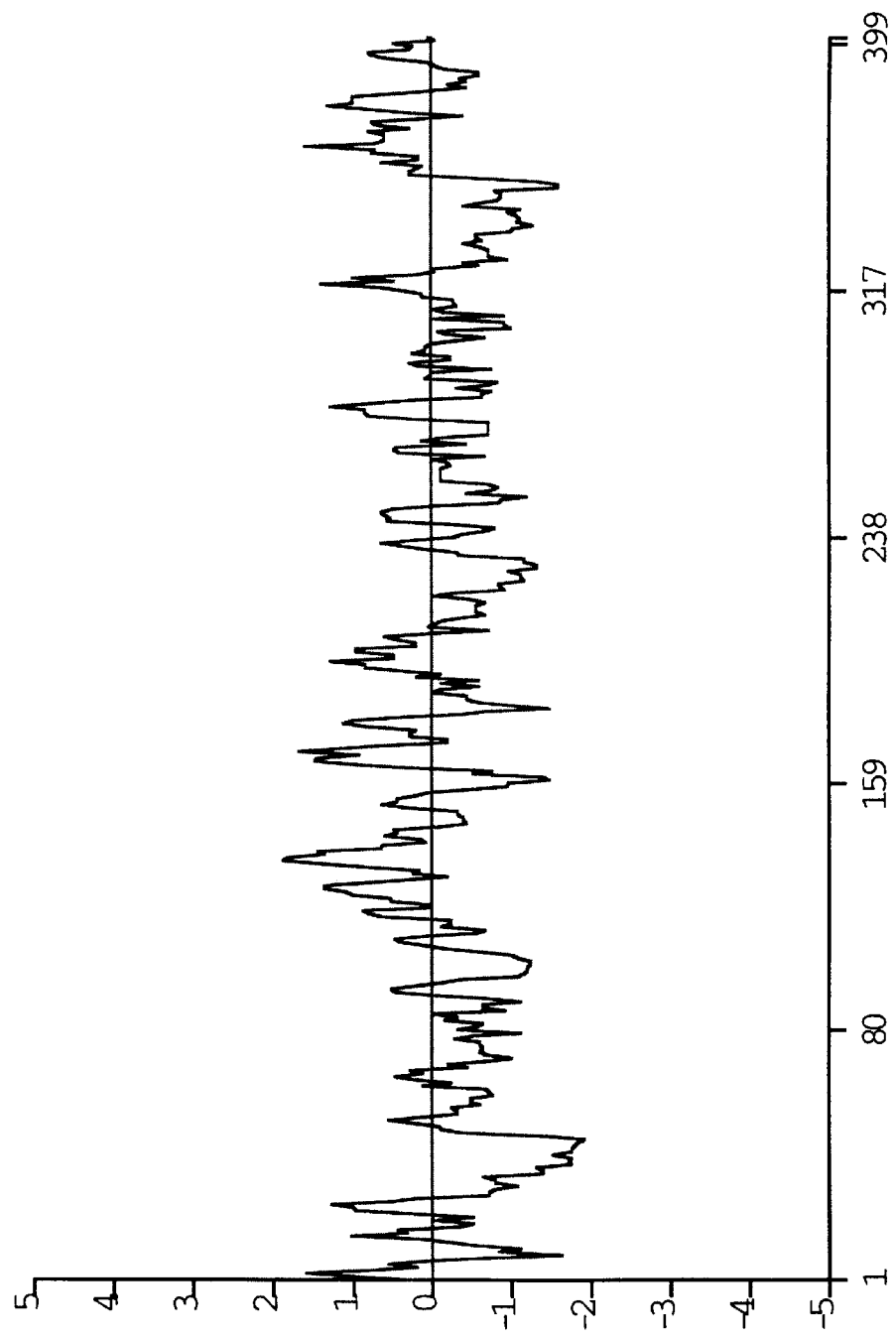
FIG. 4 shows the hydrophobicity plot for g116438, SEQ ID NO:3.

In one embodiment, the invention encompasses the novel human purinoreceptor, a polypeptide comprising the amino acid sequence of SEQ ID NO:1, as shown in FIG. 1. HPURR is 388 amino acids in length and has two potential hydrophobic transmembrane domains at residues 30–59 and 335–362, three potential sites for N-linked glycosylation at residues 153, 184, and 287, and a potential Walker type-A phosphate binding motif (Saraste, M. et al.(1990) Trends Biochem. Sci. 15:430–4) at position 325–329. As shown in FIG. 2, HPURR has chemical and structural homology with a human $P_{2X}$ receptor (g166438, SFQ ID NO:3), and two rat $P_{2X}$ receptors (g558240, SEQ ID NO:4, and g558831, SEQ ID NO:5). In particular, HPURR shares 51%, 50%, and 45% identity, respectively, with these three $P_{2X}$ receptors. As illustrated by FIGS. 3 and 4, HPURR and human $P_{2X}$ receptor g1166438 (SEQ ID NO:3), respectively, have rather similar hydrophobicity plots. Northern analysis (FIG. 5) shows the expression of this sequence in various libraries, of which 6/18 (33%) are from cells of the immune system or from tissues associated with abnormal immune responses, 4/18 (22%) are from smooth muscle, and 2/18 (11%) are from the nervous system.

The invention also encompasses HPURR variants. A preferred HPURR variant is one having at least 80%, and more preferably 90%, amino acid sequence similarity to the HPURR amino acid sequence (SEQ ID NO:1). A most preferred HPURR variant is one having at least 95% amino acid sequence similarity to SEQ ID NO:1.

The invention also encompasses polynucleotides which encode HPURR. Accordingly, any nucleic acid sequence which encodes the amino acid sequence of HPURR can be used to generate recombinant molecules which express HPURR. In a particular embodiment, the invention encompasses the polynucleotide comprising the nucleic acid of SEQ ID NO:2 as shown in FIG. 1.

It will be appreciated by those skilled in the art that as a result of the degeneracy of the genetic code, a multitude of nucleotide sequences encoding HPURR, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HPURR, and all such variations are to be considered as being specifically disclosed.

Although nucleotide sequences which encode HPURR and its variants are preferably capable of hybridizing to the nucleotide sequence of the naturally occurring HPURR under appropriately selected conditions of stringency, it may be advantageous to produce nucleotide sequences encoding HPURR or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HPURR and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode HPURR and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding HPURR or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Berger and Kimmel (1987; *Methods in Enzymology,* Vol. 152), and may be used at a defined stringency.

Altered nucleic acid sequences encoding HPURR which are encompassed by the invention include deletions, insertions, or substitutions of different nucleotides resulting in a polynucleotide that encodes the same or a functionally equivalent HPURR. The encoded protein may also contain deletions, insertions, or substitutions of amino acid residues which result in a functionally equivalent HPURR. Deliberate amino acid substitutions may be made on the basis of similarity in polarity, charge, solubility, hydrophobicity, hydrophilicity, and/or the amphipathic nature of the residues as long as the biological activity of HPURR is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding HPURR. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; M.J. Research, Watertown, Mass.) and the ABI 377 DNA sequencers (Perkin Elmer).

The polynucleotide sequence encoding HPURR may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. et al. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nuc. Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nuc. Acids Res. 19:3055–3060). Additionally, one may use PCR, nested primers, and PromoterFinder™ libraries to walk in genomic DNA (Clontech, Palo Alto, Calif.). This process avoids the need to screen libraries and may be is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-translated regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HPURR, or fusion proteins or functional equivalents thereof, may be used in recombinant DNA molecules to direct expression of HPURR, Due to the inherent degeneracy of the genetic code, other DNA sequences which encode substantially the same or a functionally equivalent amino acid sequence may be produced and these sequences may be used to clone and express HPURR.

As will be understood by those of skill in the art, it may be advantageous to produce HPURR-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the HPURR coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding HPURR may be ligated to a heterologous sequence to encode a fusion protein. For example, to screen peptide libraries for inhibitors of HPURR activity, it may be useful to encode a chimeric HPURR protein that can be recognized by a commercially available antibody. A fusion protein may also be engineered to contain a cleavage site located between a HPURR encoding sequence and the heterologous protein sequence, so that HPURR may be cleaved and purified away from the heterologous moiety.

In another embodiment, the coding sequence of HPURR may be synthesized, in whole or in part, using chemical methods well known in the art (see Caruthers, M. H. et al. (1980) Nuc. Acids Res. Symp. Ser. 215–23; Horn, T. et al. (1980) Nuc. Acids Res. Symp. Ser. 225–232). Alternatively, the protein itself may be produced using chemical methods to synthesize the HPURR amino acid sequence, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography e.g., Creighton, T. (1983) *Proteins, Structures and Molecular Principles,* W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of HPURR, or any part thereof, may be altered during direct synthesis and/or combined using chemical methods with sequences from other proteins, or any part thereof, to produce a variant polypeptide.

In order to express a biologically active HPURR, the nucleotide sequence encoding HPURR or functional equivalents, may be inserted into an appropriate expression vector, i.e., a vector which contains the necessary elements for the transcription and translation of the inserted coding sequence.

Methods which are well known to those skilled in the art may be used to construct expression vectors containing a HPURR coding sequence and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express a HPURR coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla, Calif.) or pSport1™ plasmid (Gibco BRL) and ptrp-lac hybrids, and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HPURR, vectors based on SV40 or EBV may be used with an appropriate selectable marker.

In bacterial systems, a number of expression vectors may be selected depending upon the use intended for HPURR. For example, when large quantities of HPURR are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding HPURR may be ligated into the vector in frame with sequences for the amino-terminal Met and the subsequent 7 residues of β-galactosidase so that a hybrid protein is produced; pIN vectors (Van Heeke, G. and Schuster, S. M. (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. 1987) *Methods Enzymol.* 153:516–544.

In cases where plant expression vectors are used, the expression of a sequence encoding HPURR may be driven by any of a number of promoters. For example, viral promoters such as the 35S and 19S promoters of CaMV may be used alone or in combination with the omega leader sequence from TMV Takamatsu et al. (1987) EMBO J. 6:307–311; Brisson et al. (1984) Nature 310:511–514). Alternatively, plant promoters such as the small subunit of RUBISCO or heat shock promoters may be used (Coruzzi et al. (1984) EMBO J. 3:1671–1680; Broglie et al. (1984) Science 224:838–843; Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196 or Weissbach and Weissbach (1988) *Methods for Plant Molecular Biology,* Academic Press, New York, N.Y.; pp. 421–463).

An insect system may also be used to express HPURR. For example, in one such system, *Autographa californica* nuclear polyhedrosis virus (AcNPV) is used as a vector to express foreign genes in *Spodoptera frugiperda* cells or in *Trichoplusia* larvae. The sequence encoding HPURR may be cloned into a non-essential region of the virus, such as the polyhedrin gene, and placed under control of the polyhedrin promoter. Successful insertion of HPURR will render the polyhedrin gene inactive and produce recombinant virus lacking coat protein. The recombinant viruses may then be used to infect, for example, *S. frugiperda* cells or *Trichoplusia* larvae in which HPURR may be expressed (Smith et al. (1983) J. Virol. 46:584; Engelhard, E. K. et al. (1994) Proc. Nat. Acad. Sci. 91:3224–3227).

In mammalian host cells, a number of viral-based expression systems may be utilized. In cases where an adenovirus is used as an expression vector, a sequence encoding HPURR may be ligated into an adenovirus transcription/translation complex consisting of the late promoter and tripartite leader sequence. Insertion in a non-essential E1 or E3 region of the viral genome may be used to obtain a viable virus which is capable of expressing HPURR in infected host cells (Logan and Shenk (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of a sequence encoding HPURR. Such signals include the ATG initiation codon and adjacent sequences. In cases where sequences encoding HPURR, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162; Bittner et al. (1987) *Methods Enzymol.* 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HPURR may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al. (1981) J. Mol. Biol. 150:1–14) and als or pat, which confer resistance to chlorsulfuron and phosphinotricin acetyltransferase, respectively (Murry, L. E., supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HPURR is inserted within a marker gene sequence, recombinant cells containing sequences encoding HPURR can be identified by the absence of marker gene function. Alternatively, a marker gene can be placed in tandem with a sequence encoding HPURR under the control of a single promoter. Expression of the marker gene in response to induction or selection usually indicates expression of the tandem gene as well.

Alternatively, host cells which contain the coding sequence for HPURR and express HPURR may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of the nucleic acid or protein.

The presence of the polynucleotide sequence encoding HPURR can be detected by DNA—DNA or DNA-RNA hybridization or amplification using probes or portions or fragments of polynucleotides encoding HPURR. Nucleic acid amplification based assays involve the use of oligonucleotides or oligomers based on the HPURR-encoding sequence to detect transformants containing DNA or RNA encoding HPURR. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HPURR, using either polyclonal or monoclonal antibodies specific for the protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on HPURR is preferred, but a competitive binding assay may be employed. These and other assays are described, among other places, in Hampton et al. (1990; Serological Methods, a Laboratory Manual, APS Press, St Paul, Minn.) and Maddox et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HPURR include oligolabeling, nick translation, end-labeling or PCR amplification using a labeled nucleotide. Alternatively, the sequence encoding HPURR, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding HPURR may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HPURR may be designed to contain signal sequences which direct secretion of HPURR through a prokaryotic or eukaryotic cell membrane. Other recombinant constructions may be used to join sequences encoding HPURR to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HPURR may be used to facilitate purification. One such expression vector provides for expression of a fusion protein containing HPURR, a thioredoxin or an enterokinase cleavage site, and followed by six histidine residues. The histidine residues facilitate purification on IMIAC (immobilized metal ion affinity chromatography as described in Porath, J. et al. (1992; Prot. Exp. Purif. 3: 263–281) while the enterokinase cleavage site provides a means for purifying HPURR from the fusion protein. A discussion of vectors which contain fusion proteins is provided in Kroll, D. J. et al. (1993; DNA Cell Biol. 12:441–453).

In addition to recombinant production, fragments of HPURR may be produced by direct peptide synthesis using solid-phase techniques (c. f. Stewart et al. (1969) *Solid-Phase Peptide Synthesis*, W. H. Freeman Co., San Francisco, Calif.; Merrifield, J. (1963) J. Am. Chem. Soc. 85:2149–2154). Chemical synthesis may be performed using manual techniques or by automation. Automated synthesis may be achieved, for example, using Applied Biosystems 431A Peptide Synthesizer (Perkin Elmer). Various fragments of HPURR may be chemically synthesized separately and combined using chemical methods to produce the full length molecule.

THERAPEUTICS

In another embodiment of the invention, HPURR or fragments thereof may be used for therapeutic purposes. Based on the chemical and structural homology among HPURR SEQ ID NO:1) and other $P_{2X}$ purinoreceptors (FIG. 2), and on northern analysis (FIG. 5) showing that 66% of the cDNA libraries containing HPURR transcripts are associated with cells of the immune system, smooth muscle or neurons, HPURR is believed to function in modulation of the immune response and in signaling in smooth muscle and neurons.

In one embodiment of the invention, supplying a vector expressing HPURR, or derivative thereof, may be useful in stimulating the immune response through its synergistic effects on T-cell proliferation and lysis of antigen-presenting macrophages. This would be especially useful in the treatment of immunodeficiency diseases such as AIDS in which the number of T-cells is reduced and the response to human immunodeficiency virus antigens is compromised. Control of HPURR activity as a novel approach to AIDS treatment may be especially useful in combination therapy with other antiviral agents. Such combinations of therapeutic agents having different mechanisms of action often have synergistic effects allowing the use of lower effective doses of each agent and lessening side effects.

In another embodiment, agonists of the protein, which can be identified by techniques well known to those skilled in the art, may be used to treat diseases such as thrombosis and other diseases related to excessive clot formation.

In another embodiment, antagonists or inhibitors of the protein or vectors expressing antisense sequences may be used to suppress the excessive proliferation of inflammatory cells which cause damage in immunological diseases. Such immune diseases include, but are not limited to, rheumatoid and osteoarthritis, asthma, systemic lupus., myasthenia gravis, diabetes mellitus, osteoporosis, glomerulonephritis, and scleroderma.

In another embodiment, antagonists or inhibitors of the protein or vectors expressing antisense sequences may be used to treat disorders and diseases of the nervous system resulting from altered ion transport, signal transmission, and apoptosis. Such diseases include, but are not limited to, chronic pain, neuropathic pain such as diabetic-, cancer-, and AIDS-related, neurodegenerative diseases such as Alzheimer's disease, Parkinson's disease, Huntington's disease, Creutzfeld-Jacob disease, and amyotrophic lateral sclerosis, and dementias, including AIDS-related, as well as convulsions, epilepsy, stroke, and anxiety and depression.

In another embodiment, antagonists or inhibitors of the protein or vectors expressing antisense sequencesmay be used to treat cardiovascular diseases such as angina, congestive heart failure, vasoconstriction, hypertension, atherosclerosis, restenosis, and bleeding.

In another embodiment, antagonists or inhibitors of the protein or vectors expressing antisense sequences may be used to treat disorders and diseases of the immune system such as AIDS wherein the immune response may be reduced because of excessive T-cell apoptosis.

Agonists which enhance the activity and antagonists which block or modulate the effect of HPURR may be used in those situations where such enhancement or inhibition is therapeutically desirable. Such agonists, antagonists or inhibitors may be produced using methods which are generally known in the art, and particularly involve the use of purified HPURR to produce antibodies or to screen libraries of pharmaceutical agents for those which specifically bind HPURR. For example, in one aspect, antibodies which are specific for HPURR may be used directly as an antagonist, or indirectly as a targeting or delivery mechanism for bringing a pharmaceutical agent to cells or tissue which express HPURR.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HPURR or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HPURR have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HPURR amino acids may be fused with those of another protein such as keyhole limpet hemocyanin and antibody produced against the chimeric molecule.

Monoclonal antibodies to HPURR may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1975) Nature 256:495–497; Kosbor et al. (1983) Immunol. Today 4:72; Cote et al. (1983) Proc. Natl. Acad. Sci. 80:2026–2030; Cole et al. (1985) *Monoclonal Antibodies and Cancer Therapy*, Alan R. Liss Inc., New York, N.Y., pp. 77–96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81:6851–6855; Neuberger et al. (1984) Nature 312:604–608; Takeda et al. (1985) Nature 314:452–454). Alternatively, techniques described for the production of single chain antibodies may be adapted, using methods known in the art, to produce HPURR-specific single chain antibodies. Antibodies with related specificity, but of distinct idiotypic composition, may be generated by chain shuffling from random combinatorial immunoglobin libraries (Burton, D. R. (1991) Proc. Natl. Acad. Sci. 88:11120-3).

Antibodies may also be produced by inducing in vivo production in the lymphocyte population or by screening recombinant immunoglobulin libraries or panels of highly specific binding reagents as disclosed in the literature (Orlandi et al. (1989) Proc. Natl. Acad. Sci. 86: 3833–3837; Winter, G. et al. (1991) Nature 349:293–299).

Antibody fragments which contain specific binding sites for HPURR may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 256:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HPURR and its specific antibody. A two-site, monoclonal-based immunoassay utilizing monoclonal antibodies reactive to two non-interfering HPURR epitopes is preferred, but a competitive binding assay may also be employed (Maddox, supra).

In another embodiment of the invention, the polynucleotides encoding HPURR, or any fragment thereof, or antisense sequences, may be used for therapeutic purposes. In one aspect, antisense to the polynucleotide encoding HPURR may be used in situations in which it would be desirable to block the synthesis of the protein. In particular, cells may be transformed with sequences complementary to polynucleotides encoding HPURR. Thus, antisense sequences may be used to modulate HPURR activity, or to achieve regulation of gene function. Such technology is now well known in the art, and sense or antisense oligomers or larger fragments, can be designed from various locations along the coding or control regions of sequences encoding HPURR.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HPURR. These techniques are described both in Sambrook et al. (supra) and in Ausubel et al. (supra).

Genes encoding HPURR can be turned off by transforming a cell or tissue with expression vectors which express high levels of a polynucleotide or fragment thereof which encodes HPURR. Such constructs may be used to introduce untranslatable sense or antisense sequences into a cell. Even in the absence of integration into the DNA, such vectors may continue to transcribe RNA molecules until all copies are disabled by endogenous nucleases.

Transient expression may last for a month or more with a non-replicating vector and even longer if appropriate replication elements are part of the vector system.

As mentioned above, modifications of gene expression can be obtained by designing antisense molecules, DNA, RNA or PNA, to the control regions of the gene encoding HPURR, i.e., the promoters, enhancers, and introns. Oligonucleotides derived from the transcription initiation site, e.g., between positions −10 and +10 from the 5' end of the transcript, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and Carr, B. I. *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HPURR.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HPURR. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HPURR, antibodies to HPURR, mimetics, agonists, antagonists, or inhibitors of HPURR. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HPURR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HPURR or fragments thereof, antibodies of HPURR, agonists, antagonists or inhibitors of HPURR, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HPURR may be used for the diagnosis of conditions or diseases characterized by expression of HPURR, or in assays to monitor patients being treated with HPURR, agonists, antagonists or inhibitors. The antibodies useful for diagnostic purposes may be prepared in the same manner as those described above for therapeutics. Diagnostic assays for HPURR include methods which utilize the antibody and a label to detect HPURR in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HPURR are known in the art and provide a basis for diagnosing altered or abnormal levels of HPURR expression. Normal or standard values for HPURR expression are established by combining body fluids or cell extracts taken from normal mammalian subjects, preferably human, with antibody to HPURR under conditions suitable for complex formation The amount of standard complex formation may be quantified by various methods, but preferably by photometric, means. Quantities of HPURR expressed in subject, control and disease, samples from biopsied tissues are compared with the standard values. Deviation between standard and subject values establishes the parameters for diagnosing disease.

In another embodiment of the invention, the polynucleotides encoding HPURR may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HPURR may be correlated with disease. The diagnostic assay may be used to distinguish between absence, presence, and excess expression of HPURR, and to monitor regulation of HPURR levels during therapeutic intervention.

In one aspect, hybridization with PCR probes which are capable of detecting polynucleotide sequences, including genomic sequences, encoding HPURR or closely related molecules, may be used to identify nucleic acid sequences which encode HPURR. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HPURR, alleles, or related sequences.

Probes may also be used for the detection of related sequences, and should preferably contain at least 50% of the nucleotides from any of the HPURR encoding sequences. The hybridization probes of the subject invention may be DNA or RNA and derived from the nucleotide sequence of SEQ ID NO:2 or from genomic sequence including promoter, enhancer elements, and introns of the naturally occurring HPURR.

Means for producing specific hybridization probes for DNAs encoding HPURR include the cloning of nucleic acid sequences encoding HPURR or HPURR derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HPURR may be used for the diagnosis of conditions or diseases which are associated with expression of HPURR. Examples of such conditions or diseases include immunological diseases such rheumatoid and osteoarthritis, asthma, systemic lupus, myasthenia gravis, diabetes mellitus, osteoporosis, glomerulonephritis, and scleroderma; neurological diseases including chronic pain, neuropathic pain such as diabetic-, cancer-, and AIDS-related, neurodegenerative diseases such as Alzheimer's disease, Parkinson's disease, Huntington's disease, Creutzfeld-Jacob disease, and amyotrophic lateral sclerosis, and dementias, such as AIDS-related, as well as convulsions, epilepsy, stroke, and anxiety and depression, cardiovascular diseases such as angina, congestive heart failure, vasoconstriction, hypertension, atherosclerosis, restenosis, and bleeding. The polynucleotide sequences encoding HPURR may be used in Southern or northern analysis, dot blot, or other membrane-based technologies; in PCR technologies; or in dip stick, pin, ELISA or chip assays utilizing fluids or tissues from patient biopsies to detect altered HPURR expression. Such qualitative or quantitative methods are well known in the art.

In a particular aspect, the nucleotide sequences encoding HPURR may be useful in assays that detect activation or induction of various immunological disorders, particularly those mentioned above. The nucleotide sequence encoding HPURR may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequence has hybridized with nucleotide sequences in the sample, and the presence of altered levels of nucleotide sequences encoding HPURR in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HPURR, a normal or standard profile for expression is established. This may be accomplished by combining body fluids or cell extracts taken from normal subjects, either animal or human, with a sequence, or a fragment thereof, which encodes HPURR, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to immunological diseases, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the disease.

Additional diagnostic uses for oligonucleotides encoding HPURR may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HPURR include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence which encodes HPURR may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed by Price, C. M. (1993; Blood Rev. 7:127–134), and Trask, B. J. (1991; Trends Genet. 7:149–154).

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HPURR on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HPURR, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HPURR and the agent being tested, may be measured.

Another technique for drug screening which may be used provides for high throughput screening of compounds having suitable binding affinity to the protein of interest as described in published PCT application WO84/03564. In this method, as applied to HPURR large numbers of different small test compounds are synthesized on a solid substrate, such as plastic pins or some other surface. The test compounds are reacted with HPURR, or fragments thereof, and washed. Bound HPURR is then detected by methods well known in the art. Purified HPURR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HPURR specifically compete with a test compound for binding HPURR. In this manner, the antibodies can be used to detect the presence of any peptide which shares one or more antigenic determinants with HPURR.

In additional embodiments, the nucleotide sequences which encode HPURR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I SCORNOT01 cDNA Library Construction

The cDNA library was constructed from spinal cord removed from a 71 year old, Caucasian male (lot #RA95-04-0255) obtained from the Keystone Skin Bank, International Institute for Advanced Medicine, Exton, Pa.). The tissue was flash frozen, ground in a mortar and pestle, and lysed immediately in a buffer containing guanidinium isothiocyanate. The lysate was extracted once with acid phenol, pH 4.0, once with phenol chloroform, pH 8.0, and then centrifuged over a CsCl cushion using an Beckman SW28 rotor in a L8-70M Ultracentrifuge (Beckman Instruments). The RNA was precipitated from 0.3M sodium acetate using 2.5 volumes of ethanol, resuspended in water and DNase treated for 15 min at 37° C. The poly A+ RNA was isolated using the Qiagen Oligotex kit (QIAGEN Inc, Chatsworth, Calif.) and used to construct the cDNA library.

The RNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #275105, Pharmacia), and those cDNAs exceeding 400 bp were ligated into pSport I. The plasmid pSport I was subsequently transformed into DH5a™ competent cells (Cat. #18258-012, Gibco/BRL).

II Isolation and Sequencing of cDNA Clones

Plasmid DNA was purified using the Miniprep Kit (Cat. #77468, Advanced Genetic Technologies Corporation, Gaithersburg, Md.), a 96-well block kit with reagents for 960 purifications. The recommended protocol included with the kit was employed except for the following changes. Each of the 96 wells was filled with only 1 ml of sterile Terrific Broth (Cat. #22711, LIFE TECHNOLOGIES™, Gaithersberg, Md.) with carbenicillin at 25 mg/L and glycerol at 0.4%. After the wells were inoculated, the bacteria were cultured for 24 hours and lysed with 60 $\mu$l of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger, F. and A. R. Coulson (1975; J. Mol. Biol. 94:441f), using a Hamilton Micro Lab 2200 (Hamilton, Reno, Nev.) in combination with four Peltier Thermal Cyclers (PTC200 from M.J. Research, Watertown., Mass.) and Applied Biosystems 377 or 373 DNA Sequencing Systems (Perkin Elmer), and the reading frame was determined.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993 and 1990), supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HPURR occurs. Abundance and percent abundance are also reported. Abundance directly reflects the number of times a particular transcript is represented in a cDNA library, and percent abundance is abundance divided by the total number of sequences examined in the cDNA library.

V Extension of HPURR-Encoding Polynucleotides to Full Length or to Recover Regulatory Sequences Full length HPURR-encoding nucleic acid sequence (SEQ ID NO:1) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [γ-$^{32}$p] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing 10$^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1 or Pvu II; DuPont NEN®).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the HPURR-encoding sequence, or any part thereof, is used to inhibit in vivo or in vitro expression of naturally occurring HPURR. Although use of antisense oligonucleotides, comprising about 20 base-pairs, is specifically described, essentially the same procedure is used with larger cDNA fragments. An oligonucleotide based on the coding sequences of HPURR, as shown in FIG. 1, is used to inhibit expression of naturally occurring HPURR. The complementary oligonucleotide is designed from the most unique 5' sequence as shown in FIG. 1 and used either to inhibit transcription by preventing binding to the upstream untranscribed sequence or translation of an HPURR-encoding transcript by preventing ribosomes from binding. Using an appropriate portion of the 5' sequence of SEQ ID NO:2, an effective antisense oligonucleotide includes any 15–20 nucleotides spanning the region which translates into the 5' coding sequence of the polypeptide as shown in FIG. 1.

VIII Expression of HPURR

Expression of HPURR is accomplished by subcloning the cDNA into appropriate vectors and transforming the vectors into host cells. In this case, the cloning vector, pSport, previously used for the generation of the cDNA library is used to express HPURR in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HPURR into the bacterial growth media which can be used directly in the following assay for activity.

IX Demonstration of HPURR Activity

The purinoreceptor channel-forming ability of HPURR is assayed by measuring the effect of exogenously added ATP on $Ca^{2+}$ or $Na^+$ fluxes into Xenopus oocytes that have been microinjected with messenger RNA encoding HPURR. HPURR mRNA can be synthesized in vitro using techniques well known to those skilled in the art. Methods for electrophysiological recording of ion fluxes through purinoreceptors expressed in Xenopus oocytes are well known in the art (Valera, S. et al.(1994), supra; Brake, A. J. et al, supra). The effects of known $P_{2X}$ receptor-family agonists and antagonists, such as 2-methyl-thio-ATP, γ-thio-ATP, α,β-methylene-ATP, β,γ-methylene-ATP, and suramin, can be tested by adding them singly or in combination to the oocyte bathing solution.

X Production of HPURR Specific Antibodies

HPURR that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HPURR Using Specific Antibodies

Naturally occurring or recombinant HPURR is substantially purified by immunoaffinity chromatography using antibodies specific for HPURR. An immunoaffinity column is constructed by covalently coupling HPURR antibody to an activated chromatographic resin, such as CnBr-activated Sepharose (Pharmacia & Upjohn). After the coupling, the resin is blocked and washed according to the manufacturer's instructions.

Media containing HPURR is passed over the immunoaffinity column, and the column is washed under conditions that allow the preferential absorbance of HPURR (e.g., high ionic strength buffers in the presence of detergent). The column is eluted under conditions that disrupt antibody/HPURR binding (e.g., a buffer of pH 2–3 or a high concentration of a chaotrope, such as urea or thiocyanate ion), and HPURR is collected.

XII Identification of Molecules Which Interact with HPURR

HPURR or biologically active fragments thereof are labeled with $^{125}$IBolton-Hunter reagent (Bolton et al. (1973) Biochem. J. 133:529). Candidate molecules previously arrayed in the wells of a multi-well plate are incubated with the labeled HPURR, washed and any wells with labeled HPURR complex are assayed. Data obtained using different concentrations of HPURR are used to calculate values for the number, affinity, and association of HPURR with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 388 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY:
        ( B ) CLONE: consensus ( x i ) SEQUENCE DESCRIPTION: SEQ ID NO:1:

```
Met Ala Gly Cys Cys Ala Ala Leu Ala Ala Phe Leu Phe Glu Tyr Asp
 1               5                  10                  15
Thr Pro Arg Ile Val Leu Ile Arg Ser Arg Lys Val Gly Leu Met Asn
                20                  25                  30
Arg Ala Val Gln Leu Leu Ile Leu Ala Tyr Val Ile Gly Trp Val Phe
            35                  40                  45
Val Trp Glu Lys Gly Tyr Gln Glu Thr Asp Ser Val Val Ser Ser Val
        50                  55                  60
Thr Thr Lys Val Lys Gly Val Ala Val Thr Asn Thr Ser Lys Leu Gly
65                  70                  75                  80
Phe Arg Ile Trp Asp Val Ala Asp Tyr Val Ile Pro Ala Gln Glu Glu
                85                  90                  95
Asn Ser Leu Phe Val Met Thr Asn Val Ile Leu Thr Met Asn Gln Thr
            100                 105                 110
Gln Gly Leu Cys Pro Glu Ile Pro Asp Ala Thr Thr Val Cys Lys Ser
        115                 120                 125
Asp Ala Ser Cys Thr Ala Gly Ser Ala Gly Thr His Ser Asn Gly Val
    130                 135                 140
Ser Thr Gly Arg Cys Val Ala Phe Asn Gly Ser Val Lys Thr Cys Glu
145                 150                 155                 160
Val Ala Ala Trp Cys Pro Val Glu Asp Asp Thr His Val Pro Gln Pro
                165                 170                 175
Ala Phe Leu Lys Ala Ala Glu Asn Phe Thr Leu Leu Val Lys Asn Asn
            180                 185                 190
Ile Trp Tyr Pro Lys Phe Asn Phe Ser Lys Arg Asn Ile Leu Pro Asn
        195                 200                 205
Ile Thr Thr Thr Tyr Leu Lys Ser Cys Ile Tyr Asp Ala Lys Thr Asp
    210                 215                 220
Pro Phe Cys Pro Ile Phe Arg Leu Gly Lys Ile Val Glu Asn Ala Gly
225                 230                 235                 240
His Ser Phe Gln Asp Met Ala Val Glu Gly Gly Ile Met Gly Ile Gln
                245                 250                 255
Val Asn Trp Asp Cys Asn Leu Asp Arg Ala Ala Ser Leu Cys Leu Pro
```

|     |     |     |     |     | 260 |     |     |     |     | 265 |     |     |     |     | 270 |     |     |     |
| --- | --- | --- | --- | --- | --- | --- | --- | --- | --- | --- | --- | --- | --- | --- | --- | --- | --- | --- |
| Arg | Tyr | Ser 275 | Phe | Arg | Arg | Leu | Asp 280 | Thr | Arg | Asp | Val | Glu 285 | His | Asn | Val |
| Ser | Pro 290 | Gly | Tyr | Asn | Phe | Arg 295 | Phe | Ala | Lys | Tyr | Tyr | Arg 300 | Asp | Leu | Ala |
| Gly 305 | Asn | Glu | Gln | Arg | Thr 310 | Leu | Ile | Lys | Ala | Tyr 315 | Gly | Ile | Arg | Phe | Asp 320 |
| Ile | Ile | Val | Phe | Gly 325 | Lys | Ala | Gly | Lys | Phe 330 | Asp | Ile | Ile | Pro | Thr 335 | Met |
| Ile | Asn | Ile | Gly 340 | Ser | Gly | Leu | Ala | Leu 345 | Leu | Gly | Met | Ala | Thr 350 | Val | Leu |
| Cys | Asp | Ile 355 | Ile | Val | Leu | Tyr | Cys 360 | Met | Lys | Lys | Arg | Leu 365 | Tyr | Tyr | Arg |
| Glu | Lys 370 | Lys | Tyr | Lys | Tyr | Val 375 | Glu | Asp | Tyr | Glu | Gln 380 | Gly | Leu | Ala | Ser |
| Glu 385 | Leu | Asp | Gln |

( 2 ) INFORMATION FOR SEQ ID NO:2:

( i ) SEQUENCE CHARACTERISTICS:
        ( A ) LENGTH: 1762 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY:
        ( B ) CLONE: CONSENSUS ( x i ) SEQUENCE DESCRIPTION: SEQ ID NO:2:

| | | | | | |
|---|---|---|---|---|---|
| TCGACCCACG | CGTCCGGCGG | CGCGGCCATG | GCGGGCTGCT | GCGCCGCGCT | GGCGGCCTTC | 60 |
| CTGTTCGAGT | ACGACACGCC | GCGCATCGTG | CTCATCCGCA | GCCGCAAAGT | GGGGCTCATG | 120 |
| AACCGCGCCG | TGCAACTGCT | CATCCTGGCC | TACGTCATCG | GGTGGGTGTT | TGTGTGGGAA | 180 |
| AAGGGCTACC | AGGAAACTGA | CTCCGTGGTC | AGCTCCGTTA | CGACCAAGGT | CAAGGGCGTG | 240 |
| GCTGTGACCA | ACACTTCTAA | ACTTGGATTC | CGGATCTGGG | ATGTGGCGGA | TTATGTGATA | 300 |
| CCAGCTCAGG | AGGAAAACTC | CCTCTTCGTC | ATGACCAACG | TGATCCTCAC | CATGAACCAG | 360 |
| ACACAGGGCC | TGTGCCCCGA | GATTCCAGAT | GCGACCACTG | TGTGTAAATC | AGATGCCAGC | 420 |
| TGTACTGCCG | GCTCTGCCGG | CACCCACAGC | AACGGAGTCT | CAACAGGCAG | GTGCGTAGCT | 480 |
| TTCAACGGGT | CCGTCAAGAC | GTGTGAGGTG | GCGGCCTGGT | GCCCGGTGGA | GGATGACACA | 540 |
| CACGTGCCAC | AACCTGCTTT | TTTAAAGGCT | GCAGAAAACT | TCACTCTTTT | GGTTAAGAAC | 600 |
| AACATCTGGT | ATCCCAAATT | TAATTTCAGC | AAGAGGAATA | TCCTTCCCAA | CATCACCACT | 660 |
| ACTTACCTCA | AGTCGTGCAT | TTATGATGCT | AAAACAGATC | CCTTCTGCCC | CATATTCCGT | 720 |
| CTTGGCAAAA | TAGTGGAGAA | CGCAGGACAC | AGTTTCCAGG | ACATGGCCGT | GGAGGGAGGC | 780 |
| ATCATGGGCA | TCCAGGTCAA | CTGGGACTGC | AACCTGGACA | GAGCCGCCTC | CCTCTGCTTG | 840 |
| CCCAGGTACT | CCTTCCGCCG | CCTCGATACA | CGGGACGTTG | AGCACAACGT | ATCTCCTGGC | 900 |
| TACAATTTCA | GGTTTGCCAA | GTACTACAGA | GACCTGGCTG | GCAACGAGCA | GCGCACGCTC | 960 |
| ATCAAGGCCT | ATGGCATCCG | CTTCGACATC | ATTGTGTTTG | GGAAGGCAGG | GAAATTTGAC | 1020 |
| ATCATCCCCA | CTATGATCAA | CATCGGCTCT | GGCCTGGCAC | TGCTAGGCAT | GGCGACCGTG | 1080 |
| CTGTGTGACA | TCATAGTCCT | CTACTGCATG | AAGAAAAGAC | TCTACTATCG | GGAGAAGAAA | 1140 |

```
TATAAATATG  TGGAAGATTA  CGAGCAGGGT  CTTGCTAGTG  AGCTGGACCA  GTGAGGCCTA    1200

CCCCACACCT  GGGCTCTCCA  CAGCCCCATC  AAAGAACAGA  GAGGAGGAGG  AGGGAGAAAT    1260

GGCCACCACA  TCACCCCAGA  GAAATTTCTG  GAATCTGATT  GAGTTTCCAC  TCCACAAGCA    1320

CTCAGGGTTC  CCCAGCAGCT  CCTGTGTGTT  GTGTGCAGGA  TTTGTTTGCC  CACTCGGCCC    1380

AGGAGGTCAG  CAGTCTGTTC  TTGGCTGGGT  CAACTTTGCT  TTTCCCGCAA  CCTGGGGTTG    1440

TCGGGGGAGC  GCTGGCCCGA  CGCAGTGGCA  CTGCTGTGGC  TTTCAGGGCT  GGAGCTGGCT    1500

TTGTTCAGAA  GCCTCCTGTC  TCCAGCTCTT  TACAGGACAG  GCCCAGTCCT  TGAGGCACG     1560

GCGGCTCTGT  TCAAGCACTT  TATGCGGCAG  GGGAGGCCGC  CTGGCTGCAG  TCACTAGACT    1620

TGTAGCAGGC  CTGGGCTGCA  GGCTTCCCCC  CGACCATTCC  CTGCAGCCAT  GCGGCAGAGC    1680

TGGCATTTCT  CCTCAGAGAA  GCGCTGTGCT  AAGGTGATCG  AGGACCAGAC  ATTAAAGCGT    1740

GATTTTCTTA  AAAAAAAAA   AA                                                1762
```

( 2 ) INFORMATION FOR SEQ ID NO:3:

( i ) SEQUENCE CHARACTERISTICS:
        ( A ) LENGTH: 399 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 166438

( x i ) SEQUENCE DESCRIPTION: SEQ ID NO:3:

```
Met  Ala  Arg  Arg  Phe  Gln  Glu  Glu  Leu  Ala  Ala  Phe  Leu  Phe  Glu  Tyr
 1                   5                        10                       15

Asp  Thr  Pro  Arg  Met  Val  Leu  Val  Arg  Asn  Lys  Lys  Val  Gly  Val  Ile
              20                       25                       30

Phe  Arg  Leu  Ile  Gln  Leu  Val  Val  Leu  Val  Tyr  Val  Ile  Gly  Trp  Val
              35                       40                       45

Phe  Leu  Tyr  Glu  Lys  Gly  Tyr  Gln  Thr  Ser  Ser  Gly  Leu  Ile  Ser  Ser
         50                       55                       60

Val  Ser  Val  Lys  Leu  Lys  Gly  Leu  Ala  Val  Thr  Gln  Leu  Pro  Gly  Leu
 65                       70                       75                       80

Gly  Pro  Gln  Val  Trp  Asp  Val  Ala  Asp  Tyr  Val  Phe  Pro  Ala  Gln  Gly
                    85                       90                       95

Asp  Asn  Ser  Phe  Val  Val  Met  Thr  Asn  Phe  Ile  Val  Thr  Pro  Lys  Gln
              100                      105                      110

Thr  Gln  Gly  Tyr  Cys  Ala  Glu  His  Pro  Glu  Gly  Gly  Ile  Cys  Lys  Glu
              115                      120                      125

Asp  Ser  Gly  Cys  Thr  Pro  Gly  Lys  Ala  Lys  Arg  Lys  Ala  Gln  Gly  Ile
         130                      135                      140

Arg  Thr  Gly  Lys  Cys  Val  Ala  Phe  Asn  Asp  Thr  Val  Lys  Thr  Cys  Glu
145                       150                      155                      160

Ile  Phe  Gly  Trp  Cys  Pro  Val  Glu  Val  Asp  Asp  Ile  Pro  Arg  Pro
                   165                      170                      175

Ala  Leu  Leu  Arg  Glu  Ala  Glu  Asn  Phe  Thr  Leu  Phe  Ile  Lys  Asn  Ser
              180                      185                      190

Ile  Ser  Phe  Pro  Arg  Phe  Lys  Val  Asn  Arg  Arg  Asn  Leu  Val  Glu  Glu
              195                      200                      205

Val  Asn  Ala  Ala  His  Met  Lys  Thr  Cys  Leu  Phe  His  Lys  Thr  Leu  His
```

```
                    210                          215                          220
Pro   Leu   Cys   Pro   Val   Phe   Gln   Leu   Gly   Tyr   Val   Gln   Glu   Ser   Gly
225                     230                          235                          240

Gln   Asn   Phe   Ser   Thr   Leu   Ala   Glu   Lys   Gly   Val   Val   Gly   Ile   Thr
                        245                          250                          255

Ile   Asp   Trp   His   Cys   Asp   Leu   Asp   Trp   His   Val   Arg   His   Cys   Arg   Pro
                  260                          265                          270

Ile   Tyr   Glu   Phe   His   Gly   Leu   Tyr   Glu   Glu   Lys   Asn   Leu   Ser   Pro   Gly
            275                          280                          285

Phe   Asn   Phe   Arg   Phe   Ala   Arg   His   Phe   Val   Glu   Asn   Gly   Thr   Asn   Tyr
      290                          295                          300

Arg   His   Leu   Phe   Lys   Val   Phe   Gly   Ile   Arg   Phe   Asp   Ile   Leu   Val   Asp
305                           310                          315                          320

Gly   Lys   Ala   Gly   Lys   Phe   Asp   Ile   Ile   Pro   Thr   Met   Thr   Thr   Ile   Gly
                        325                          330                          335

Ser   Gly   Ile   Gly   Ile   Phe   Gly   Val   Ala   Thr   Val   Leu   Cys   Asp   Leu   Leu
                  340                          345                          350

Leu   Leu   His   Ile   Leu   Pro   Lys   Arg   His   Tyr   Tyr   Lys   Gln   Lys   Lys   Phe
            355                          360                          365

Lys   Tyr   Ala   Glu   Asp   Met   Gly   Pro   Gly   Ala   Ala   Glu   Arg   Asp   Leu   Ala
      370                          375                          380

Ala   Thr   Ser   Ser   Thr   Leu   Gly   Leu   Gln   Glu   Asn   Met   Arg   Thr   Ser
385                           390                          395
```

( 2 ) INFORMATION FOR SEQ ID NO:4:

( i ) SEQUENCE CHARACTERISTICS:
            ( A ) LENGTH: 399 amino acids
            ( B ) TYPE: amino acid
            ( C ) STRANDEDNESS: single
            ( D ) TOPOLOGY: linear ( i i ) MOLECULE TYPE: peptide ( v i i ) IMMEDIATE SOURCE:
            ( A ) LIBRARY: GenBank
            ( B ) CLONE: 558240

( x i ) SEQUENCE DESCRIPTION: SEQ ID NO:4:

```
Met   Ala   Arg   Arg   Leu   Gln   Asp   Glu   Leu   Ser   Ala   Phe   Phe   Phe   Glu   Tyr
1                       5                          10                           15

Asp   Thr   Pro   Arg   Met   Val   Leu   Val   Arg   Asn   Lys   Lys   Val   Gly   Val   Ile
                        20                           25                           30

Phe   Arg   Leu   Ile   Gln   Leu   Val   Val   Leu   Val   Tyr   Val   Ile   Gly   Trp   Val
            35                           40                           45

Phe   Val   Tyr   Glu   Lys   Gly   Tyr   Gln   Thr   Ser   Ser   Asp   Leu   Ile   Ser   Ser
      50                           55                           60

Val   Ser   Val   Lys   Leu   Lys   Gly   Leu   Ala   Val   Thr   Gln   Leu   Gln   Gly   Leu
65                            70                           75                           80

Gly   Pro   Gln   Val   Trp   Asp   Val   Ala   Asp   Tyr   Val   Phe   Pro   Ala   His   Gly
                        85                           90                           95

Asp   Ser   Ser   Phe   Val   Val   Met   Thr   Asn   Phe   Ile   Val   Thr   Pro   Gln   Gln
                  100                          105                          110

Thr   Gln   Gly   His   Cys   Ala   Glu   Asn   Pro   Glu   Gly   Gly   Ile   Cys   Gln   Asp
            115                          120                          125

Asp   Ser   Gly   Cys   Thr   Pro   Gly   Lys   Ala   Glu   Arg   Lys   Ala   Gln   Gly   Ile
      130                          135                          140

Arg   Thr   Gly   Asn   Cys   Val   Pro   Phe   Asn   Gly   Thr   Val   Lys   Thr   Cys   Glu
```

|     |     |     |     | 145 |     |     |     | 150 |     |     |     | 155 |     |     |     | 160 |
|-----|-----|-----|-----|-----|-----|-----|-----|-----|-----|-----|-----|-----|-----|-----|-----|-----|

Ile Phe Gly Trp Cys Pro Val Glu Val Asp Lys Ile Pro Ser Pro
                      165                  170                  175

Ala Leu Leu Arg Glu Ala Glu Asn Phe Thr Leu Phe Ile Lys Asn Ser
            180                  185                  190

Ile Ser Phe Pro Arg Phe Lys Val Asn Arg Arg Asn Leu Val Glu Glu
        195                  200                  205

Val Asn Gly Thr Tyr Met Lys Lys Cys Leu Tyr His Lys Ile Gln His
        210                  215                  220

Pro Leu Cys Pro Val Phe Asn Leu Gly Tyr Val Val Arg Glu Ser Gly
225                    230                  235                  240

Gln Asp Phe Arg Ser Leu Ala Glu Lys Gly Gly Val Val Gly Ile Thr
            245                250                  255

Ile Asp Trp Lys Cys Asp Leu Asp Trp His Val Arg His Cys Lys Pro
        260                  265                  270

Ile Tyr Gln Phe His Gly Leu Tyr Gly Glu Lys Asn Leu Ser Pro Gly
            275                280                  285

Phe Asn Phe Arg Phe Ala Arg His Phe Val Gln Asn Gly Thr Asn Arg
    290                  295                  300

Arg His Leu Phe Lys Val Phe Gly Ile His Phe Asp Ile Leu Val Asp
305                    310                  315                  320

Gly Lys Ala Gly Lys Phe Asp Ile Ile Pro Thr Met Thr Thr Ile Gly
                325                330                335

Ser Gly Ile Gly Ile Phe Gly Val Ala Thr Val Leu Cys Asp Leu Leu
            340                345                350

Leu Leu His Ile Leu Pro Lys Arg His Tyr Tyr Lys Gln Lys Lys Phe
        355                  360                  365

Lys Tyr Ala Glu Asp Met Gly Pro Gly Glu Gly Glu His Asp Pro Val
        370                  375                  380

Ala Thr Ser Ser Thr Leu Gly Leu Gln Glu Asn Met Arg Thr Ser
385                    390                  395

( 2 ) INFORMATION FOR SEQ ID NO:5:

( i ) SEQUENCE CHARACTERISTICS:
        ( A ) LENGTH: 472 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 558831

( x i ) SEQUENCE DESCRIPTION: SEQ ID NO:5:

Met Val Arg Arg Leu Ala Arg Gly Cys Trp Ser Ala Phe Trp Asp Tyr
1                  5                  10                  15

Glu Thr Pro Lys Val Ile Val Val Arg Asn Arg Arg Leu Gly Phe Val
            20                25                  30

His Arg Met Val Gln Leu Leu Ile Leu Leu Tyr Phe Val Trp Tyr Val
        35                  40                  45

Phe Ile Val Gln Lys Ser Tyr Gln Asp Ser Glu Thr Gly Pro Glu Ser
        50                  55                  60

Ser Ile Ile Thr Lys Val Lys Gly Ile Thr Met Ser Glu Asp Lys Val
65                    70                  75                  80

Trp Asp Val Glu Glu Tyr Val Lys Pro Pro Glu Gly Gly Ser Val Val

-continued

|   |   |   |   | 85 |   |   |   | 90 |   |   |   | 95 |   |   |
|---|---|---|---|---|---|---|---|---|---|---|---|---|---|---|
| Ser | Ile | Ile | Thr<br>100 | Arg | Ile | Glu | Val | Thr<br>105 | Pro | Ser | Gln | Thr | Leu<br>110 | Gly | Thr |
| Cys | Pro | Glu<br>115 | Ser | Met | Arg | Val | His<br>120 | Ser | Ser | Thr | Cys | His<br>125 | Ser | Asp | Asp |
| Asp | Cys<br>130 | Ile | Ala | Gly | Gln | Leu<br>135 | Asp | Met | Gln | Gly | Asn<br>140 | Gly | Ile | Arg | Thr |
| Gly<br>145 | His | Cys | Val | Pro | Tyr<br>150 | Tyr | His | Gly | Asp | Ser<br>155 | Lys | Thr | Cys | Glu | Val<br>160 |
| Ser | Ala | Trp | Cys | Pro<br>165 | Val | Glu | Asp | Gly | Thr<br>170 | Ser | Asp | Asn | His | Phe<br>175 | Leu |
| Gly | Lys | Met | Ala<br>180 | Pro | Asn | Phe | Thr | Ile<br>185 | Leu | Ile | Lys | Asn | Ser<br>190 | Ile | His |
| Tyr | Pro | Lys<br>195 | Phe | Lys | Phe | Ser | Lys<br>200 | Gly | Asn | Ile | Ala | Ser<br>205 | Gln | Lys | Ser |
| Asp | Tyr<br>210 | Leu | Lys | His | Cys | Thr<br>215 | Phe | Asp | Gln | Asp | Ser<br>220 | Asp | Pro | Tyr | Cys |
| Pro<br>225 | Ile | Phe | Arg | Leu | Gly<br>230 | Phe | Ile | Val | Glu | Lys<br>235 | Ala | Gly | Glu | Asn | Phe<br>240 |
| Thr | Glu | Leu | Ala | His<br>245 | Lys | Gly | Gly | Val | Ile<br>250 | Gly | Val | Ile | Ile<br>255 | Asn | Trp |
| Asn | Cys | Asp | Leu<br>260 | Asp | Leu | Ser | Glu | Ser<br>265 | Glu | Cys | Asn | Pro | Lys<br>270 | Tyr | Ser |
| Phe | Arg | Arg<br>275 | Leu | Asp | Pro | Lys | Tyr<br>280 | Asp | Pro | Ala | Ser | Ser<br>285 | Gly | Tyr | Asn |
| Phe | Arg<br>290 | Phe | Ala | Lys | Tyr | Tyr<br>295 | Lys | Ile | Asn | Gly | Thr<br>300 | Thr | Thr | Thr | Arg |
| Thr<br>305 | Leu | Ile | Lys | Ala | Tyr<br>310 | Gly | Ile | Arg | Ile | Asp<br>315 | Val | Ile | Val | His | Gly<br>320 |
| Gln | Ala | Gly | Lys | Phe<br>325 | Ser | Leu | Ile | Pro | Thr<br>330 | Ile | Ile | Asn | Leu | Ala<br>335 | Thr |
| Ala | Leu | Thr | Ser<br>340 | Ile | Gly | Val | Gly | Ser<br>345 | Phe | Leu | Cys | Asp | Trp<br>350 | Ile | Leu |
| Leu | Thr | Phe<br>355 | Met | Asn | Lys | Asn | Lys<br>360 | Leu | Tyr | Ser | His | Lys<br>365 | Lys | Phe | Asp |
| Lys | Val | Arg<br>370 | Thr | Pro | Lys | His<br>375 | Pro | Ser | Ser | Arg | Trp<br>380 | Pro | Val | Thr | Leu |
| Ala<br>385 | Leu | Val | Leu | Gly | Gln<br>390 | Ile | Pro | Pro | Pro<br>395 | Ser | His | Tyr | Ser | Gln<br>400 |
| Asp | Gln | Pro | Pro | Ser<br>405 | Pro | Pro | Ser | Gly | Glu<br>410 | Gly | Pro | Thr | Leu | Gly<br>415 | Glu |
| Gly | Ala | Glu | Leu<br>420 | Pro | Leu | Ala | Val | Gln<br>425 | Ser | Pro | Arg | Pro | Cys<br>430 | Ser | Ile |
| Ser | Ala | Leu<br>435 | Thr | Glu | Gln | Val | Val<br>440 | Asp | Thr | Leu | Gly | Gln<br>445 | His | Met | Gly |
| Gln | Arg<br>450 | Pro | Pro | Val | Pro<br>455 | Glu | Pro | Ser | Gln | Asp<br>460 | Ser | Thr | Ser | Thr |
| Asp<br>465 | Pro | Lys | Gly | Leu | Ala<br>470 | Gln | Leu |   |   |   |   |   |   |   |   |

What is claimed is:

1. An isolated and purified polynucleotide molecule encoding the amino acid sequence of SEQ ID NO:1.

2. A hybridization probe comprising the polynucleotide molecule of claim 1.

3. An expression vector containing the polynucleotide molecule of claim 1.

4. A host cell containing the expression vector of claim 3.

5. A method for producing a polypeptide comprising the amino acid sequence of SEQ ID NO:1, the method comprising the steps of:
   a) culturing the host cell of claim 4 under conditions suitable for the expression of the polypeptide; and
   b) recovering the polypeptide from the host cell culture.

6. An isolated and purified polynucleotide molecule comprising SEQ ID NO:2.

7. An isolated and purified polynucleotide molecule comprising a sequence which is complementary to SEQ ID NO:2.

8. A hybridization probe comprising the polynucleotide molecule of claim 7.

* * * * *